United States Patent [19]
Smith

[11] Patent Number: 5,626,594
[45] Date of Patent: May 6, 1997

[54] KERATOSCOPIC SURGICAL INSTRUMENT FOR MAKING RADIAL AND ARCUATE CORNEAL INCISIONS

[76] Inventor: Alan D. Smith, 5757 Colorado Ave., Odessa, Tex. 79762

[21] Appl. No.: 574,615

[22] Filed: Dec. 19, 1995

Related U.S. Application Data

[62] Division of Ser. No. 151,996, Nov. 15, 1993, Pat. No. 5,486,188.

[51] Int. Cl.$^6$ .................................................. A61B 17/32
[52] U.S. Cl. ............................................ 606/166; 606/167
[58] Field of Search ............................... 606/166, 167, 606/170, 174, 180, 172; 30/2, 320, 338, 294

[56] References Cited

U.S. PATENT DOCUMENTS

| | | | |
|---|---|---|---|
| 4,744,362 | 5/1988 | Gründler | 606/166 |
| 4,750,489 | 6/1988 | Berkman et al. | 606/166 |
| 4,768,509 | 9/1988 | Grosvenor et al. | 606/166 |
| 5,447,517 | 9/1995 | Steen et al. | 606/166 |

*Primary Examiner*—Michael Powell Buiz
*Assistant Examiner*—William Lewis
*Attorney, Agent, or Firm*—Akin, Gump, Strauss, Hauer & Feld, L.L.P.

[57] ABSTRACT

An incision guide instrument for radial keratotomy has a lens positionable over a cornea, containing an incision guide slot adjacent to which is disposed two mirror surfaces within the lens. The mirrors are angled to allow a surgeon to observe and control the blade depth penetration into the cornea. The slotted, mirrored lens is rotatable and has clip and notch means to locate any of sixteen different radial incision positions. Transverse arcuate cuts are also allowed by the rotatable lens, and a stop means prevents the transverse cuts from contacting the radial cuts. An annular cone disposed over the sclera defines a vacuum chamber for holding the eye in position relative to the lens.

18 Claims, 9 Drawing Sheets

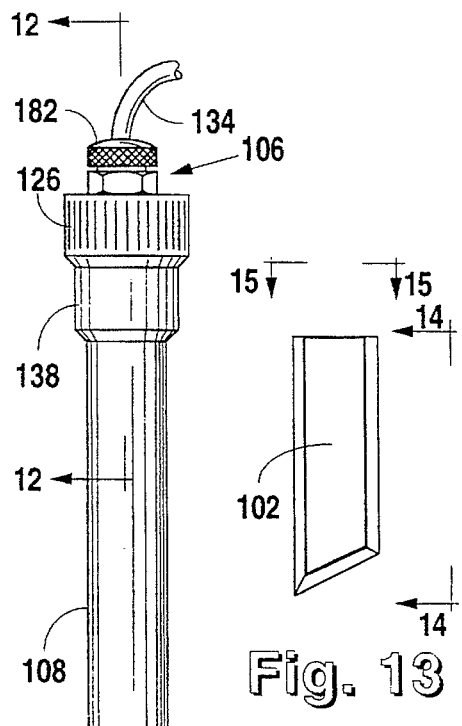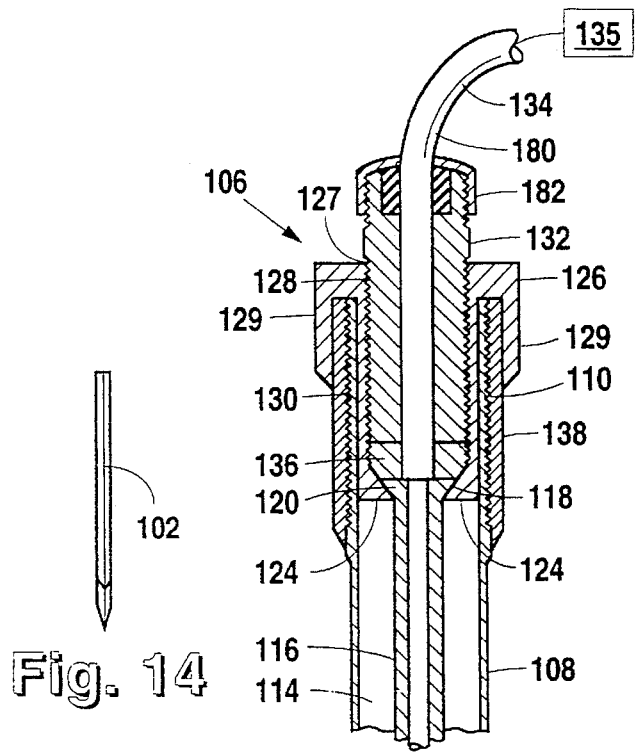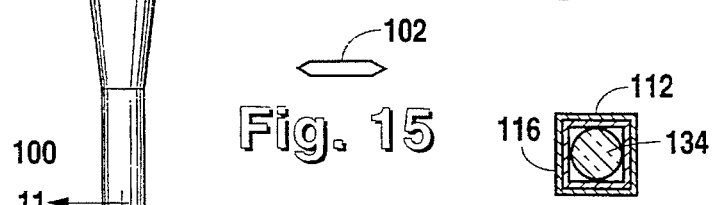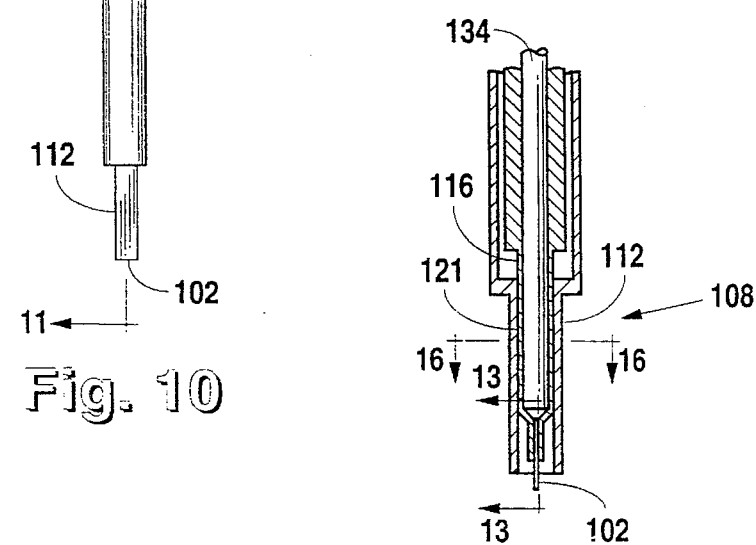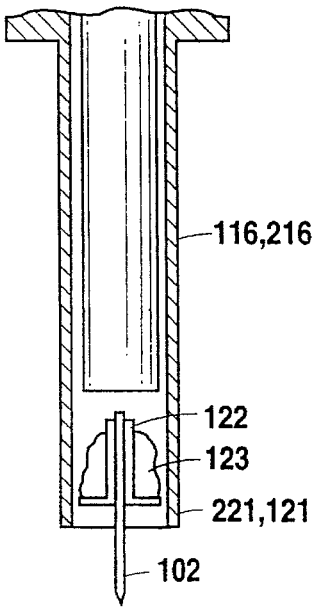

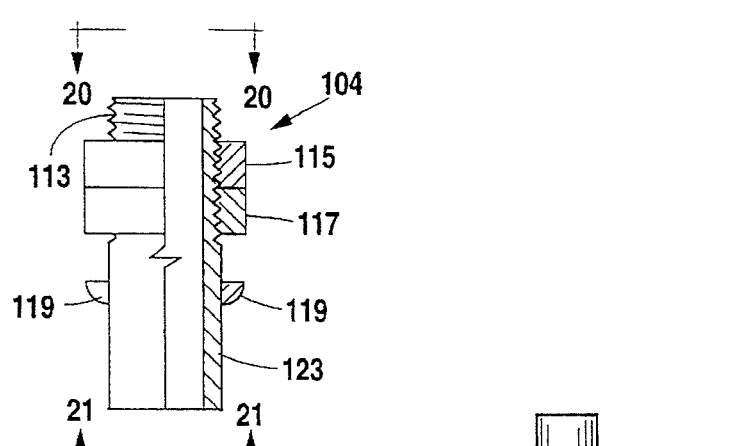
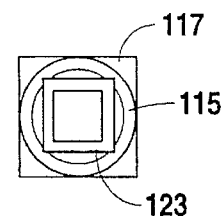
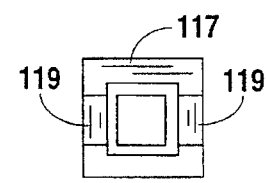
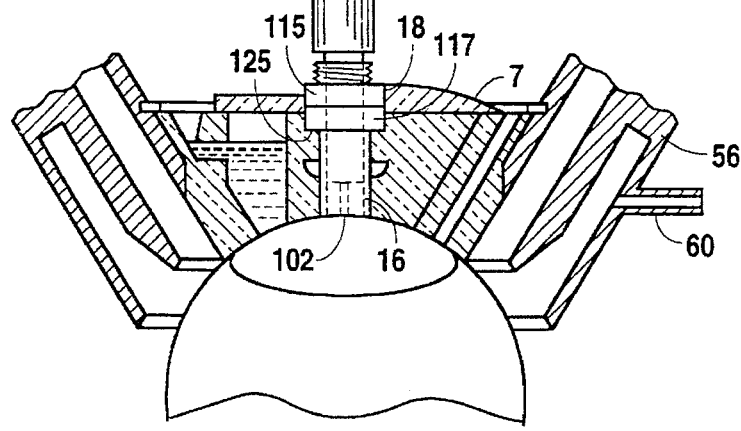
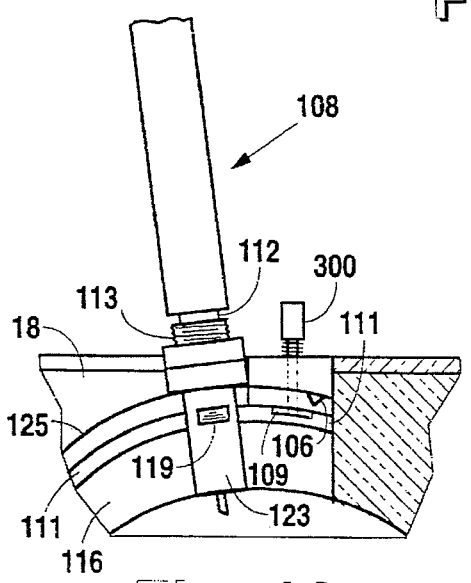
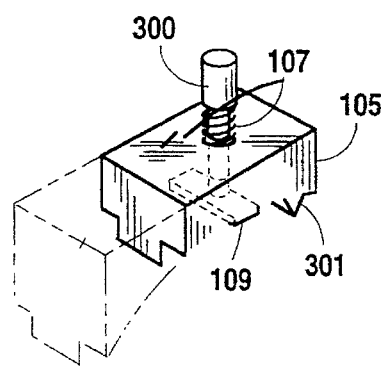

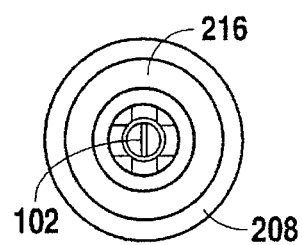
Fig. 25
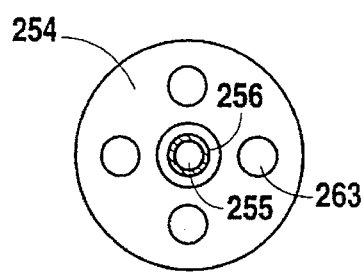
Fig. 26
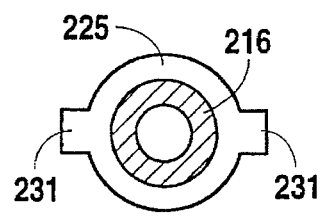
Fig. 28
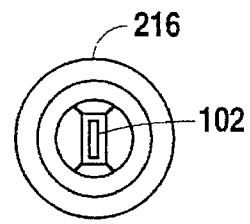
Fig. 29
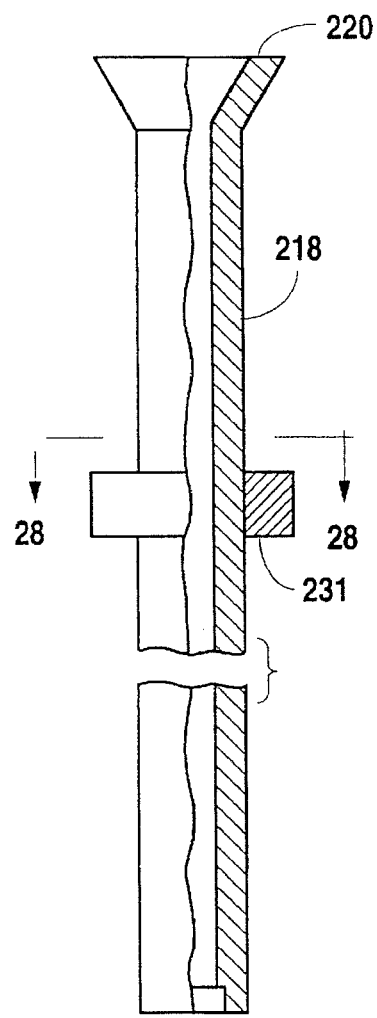
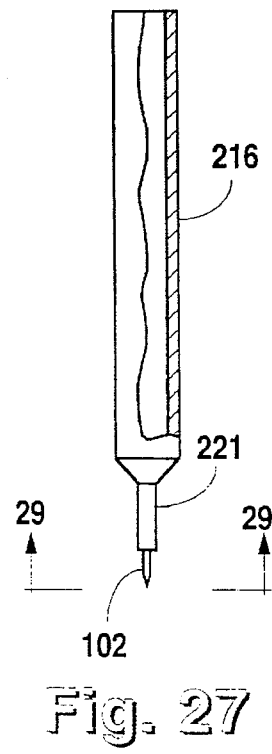
Fig. 27

KERATOSCOPIC SURGICAL INSTRUMENT FOR MAKING RADIAL AND ARCUATE CORNEAL INCISIONS

This is a divisional of application Ser. No. 08/151,996 filed 15 Nov. 1993 now U.S. Pat. No. 5,486,188.

BACKGROUND OF THE INVENTION

1. Field of the Invention

The present invention generally relates to corneal surgery, and is more specifically directed to an instrument including a lens having a linear incision guide for use in radial keratotomy procedures for reducing myopia and a tangential incision guide for effecting tangentially oriented incisions for astigmatic corrections. In both procedures precise control of incision depth is achieved by use of a mirror adjacent the incision area for permitting the surgeon to visually confirm and guide the corneal penetration depth of the scalpel being used.

2. Prior Art

Prior art devices do not allow the surgeon to control the incision depth by direct observation. In the prior art, the use of ultrasonic devices to measure the thickness of the cornea prior to surgery has been commonly used in an effort to afford the surgeon an indication of the corneal thickness. Such measurements, however, are plagued by significant errors because of the extremely small dimensions involved, leading to the currently observed and unacceptably high rates of corneal perforation.

Both radial and astigmatic keratotomy determine corneal cutting depth by use of an ultrasonic pachymeter, which maps corneal thickness in multiple locations on the cornea. Blade cutting depths approximately 98% of corneal thickness are usually required to produce desired corneal flattening and the tolerance for blade depth accuracy may be only as little as 5 microns. Unfortunately, the use of an ultrasonic pachymeter to set blade depth can result in large errors in incisional depth so that both overly shallow and excessively deep incisions are common. Thus perforations of the cornea are common as are overly shallow radial or transverse incisions which often reduce the effectiveness of the procedures. In fact, the inaccuracy of this step in these procedures is exemplified by the fact that the blade depth is usually set at 20 to 35 microns deeper than the ultrasonically measured corneal thickness in an effort to produce the desired effect.

Although radial and astigmatic keratotomy are facilitated by various radial, transverse and optical zone markers, the procedures are currently done free handed frequently producing errors in incision placement, incision length, incision direction and often inadvertent extension of radial incisions into the optical zone. Moreover, transverse corneal cuts often inadvertently extend into adjacent radial incisions, causing irregular astigmatism and wound gape.

The use of a slotted template as a guide for incisions in radial keratotomy surgery is known in the art; however, the procedures are currently done free handed in many instances. All of the teachings of the prior art, however, suffer from one or more flaws regarding inadequate control of the penetration depth and position of the incision.

U.S. Pat. No. 4,815,463 to Hanna discloses an apparatus for radial keratotomy surgery. The device uses a rigid template lens that fits against the surface of the cornea, molding it to the proper shape. The template lens has a plurality of slots for guiding the blades, and fits within a conical base member that is placed over the eye of the patient. The apparatus uses a vacuum to secure the cornea to the template. The incision blades are integrated directly into the device, and may be adjusted to vary the depth of the incision along the length of the cut. All incisions are made simultaneously.

U.S. Pat. No. 4,724,837 to Gannon discloses an apparatus and method for performing radial keratotomy surgery, the apparatus consisting of a cylindrical tubular housing, the lower end of which has a rigid multi-slotted incision guide template that fits against the cornea and conforms it to the proper shape. Scalpel blades are integrated into the device, and all incisions are made simultaneously.

A spring-loaded plunger brings the blades into contact with the cornea. Initial incision depth is set by adjusting the plunger stroke length. A second multi-slotted template is aligned with the corneal template to vary incision depth along the length of the cut. Roller bearings mounted on the sides of the blades contact the second template as the plunger is depressed, urging the blades outward from the center of the cornea to the ends of the template slots. By changing the thickness of the second template, the depth of incision can be varied along the length of the cut.

U.S. Pat. No. 4,688,570 to Kramer et al. discloses a simple, multi-slotted incision guide template for radial keratotomy surgery fitting directly onto the surface of a cornea and conforming it to the template's shape. The device has a cylindrical body, with inner and outer walls forming an annular chamber in which a vacuum is created to anchor the device.. to the eye. The device is employed in conjunction with a scalpel blade having guards which contact the upper surface of the template to prevent excessive incision depth.

U.S. Pat. No. 4,619,259 to Graybill et al. is directed to a device for radial keratotomy surgery having a slotted template guide that fits directly onto the cornea and conforms it to the shape of the template. Scalpel blades are integrated into the device in the form of a bladed disc positioned perpendicularly to the visual axis of the eye. The blades are actuated manually by a micrometer plunger assembly. Vacuum is used to ensure the device fits snugly onto the surface of the eye.

U.S. Pat. No. 4,526,171 to Schachar reveals a corneal incision device having a multi-slotted guide template, the lower surface of which holds the cornea in place and molds it to conform to the shape of the template. Used in conjunction with the device is a bladed disc, the depth of incision being controlled by a screw micrometer which advances the blades toward the incision guide and into the cornea. The bladed disc is spring-loaded to automatically retract when the screw micrometer is reversed.

U.S. Pat. No. 4,406,285 to Villasenor et al. discloses a template guide fitting over the surface of a cornea and conforming it to the shape of the template. Thickness of the template varies inversely with the thickness of the cornea immediately underneath it; the varying thickness controls blade depth penetration. Finger and thumb grips enable the operator to position the device over the eye.

Thus, a common problem with all of the prior art devices is that they do not permit continuous and/or accurate monitoring of the depth of the incision while the incision is being effected.

It is consequently the primary object of the present invention to provide new and improved means for permitting visual monitoring of incision depth in keratotomy surgery.

A further object of the present invention is a provision of new and improved means for accurately positioning radial and tangential incisions during keratotomy surgery.

Yet another object of the present invention is the provision of new and improved apparatus and methods for preventing tangential incisions from intersecting radial incisions during keratotomy procedures.

Another object of the invention is the provision of means for permitting the obtainment of precise desired corneal penetration during keratotomy procedures.

SUMMARY OF THE INVENTION

The present invention is directed to achieving the foregoing objects and overcoming the problems heretofore endemic in radial keratotomy, by achieving sufficiently precise control of the depth of corneal penetration of the scalpel blade to significantly reduce the incidence of corneal perforation associated with radial and astigmatic keratotomy surgery and by providing optimal accuracy in the depth, placement and length of all incisions.

According to the first embodiment of the present invention, a guide lens template having a scalpel receiving slot for permitting the making of an incision and a concave spherical surface on one face is placed over the cornea of the eye, with the concave spherical surface engaging the cornea and causing the cornea to conform to the shape of the concave spherical surface. The guide lens fits telescopically and concentrically within an annular, inverted cone rotatable about the central axis of the cone. Two nonrotatable lower support cones maintain the instrument in a fixed position relative to the cornea. Control of the incision depth is achieved by visual monitoring of the incision by two mirror surfaces located within the guide lens. The mirror surfaces are parallel to the linear direction of the slot, but angled with respect to the plane formed by the slot means. A source of illumination allows the surgeon to use the mirror surfaces to constantly visually inspect the depth of the incision during the entire incision procedure.

Before an incision is made, the axis of the guide template is aligned with the visual axis of the eye by the adjustment of eccentric alignment rings angularly disposed around the rotatable cone. To make a radial incision, the incision slot is placed in a desired radial position along the periphery of the eye by rotating the rotatable cone which houses the guide lens. The incision is made manually by a scalpel using the slot as a guide means. The surgeon manually adjusts stop means on the knife to preset the maximum penetration depth of the knife before beginning the incision. It is also possible to use the instrument to make arcuate cuts in the segments extending between but not intersecting the radial cuts for correcting astigmatism.

BRIEF DESCRIPTION OF THE DRAWINGS

The subject matter of the invention as summarized above and described in detail below is better understood in reference to the accompanying drawings in which:

FIG. 10 is a front elevation view of self-illuminated scalpel means employed with the apparatus illustrated in FIGS. 1–9;

FIG. 11 is a sectional view taken along lines 11—11 of FIG. 10;

FIG. 11A is a partial sectional view of the lower portion of the scalpel;

FIG. 12 is a sectional view taken along lines 12—12 of FIG. 10;

FIG. 13 is a side elevation view of a blade of the scalpel of FIGS. 10, 11 and 12;

FIG. 14 is a sectional view taken along lines 14—14 of FIG. 13;

FIG. 15 is a sectional view taken along lines 15—15 of FIG. 13;

FIG. 16 is a sectional view taken along lines 16—16 of FIG. 11;

FIG. 17 is an enlarged view taken along the same section as FIG. 4 and illustrating the scalpel in position in the lens for effecting a radial incision in the cornea of the eye;

FIG. 18 is a sectional view taken along lines 18—18 of FIG. 4;

FIG. 19 is a front elevation view partially in section of scalpel blocking means operable for fixedly positioning the scalpel in the transverse guide slot of the support lens for effecting arcuate incisions;

FIG. 20 is a view of the scalpel locking means of FIG. 19 taken along lines 20—20 of FIG. 19;

FIG. 21 is a view of the scalpel locking means of FIG. 19 taken along lines 21—21 of FIG. 19;

FIG. 22 is a perspective view of scalpel movement limiting abutment means positionable in the guide slot of the lens for limiting extent of possible movement there along;

FIG. 25 is a sectional view looking in the direction of arrows 25—25 of FIG. 23;

FIG. 26 is a sectional view taken along lines 26—26 of FIG. 24;

FIG. 27 is a partial sectional view of the lower portion of the second embodiment scalpel of FIG. 23;

FIG. 28 is a sectional view taken along lines 28—28 of FIG. 27: and

FIG. 29 is a view taken along lines 29—29 of FIG. 27.

DESCRIPTION OF THE FIRST EMBODIMENT

Figure 2:
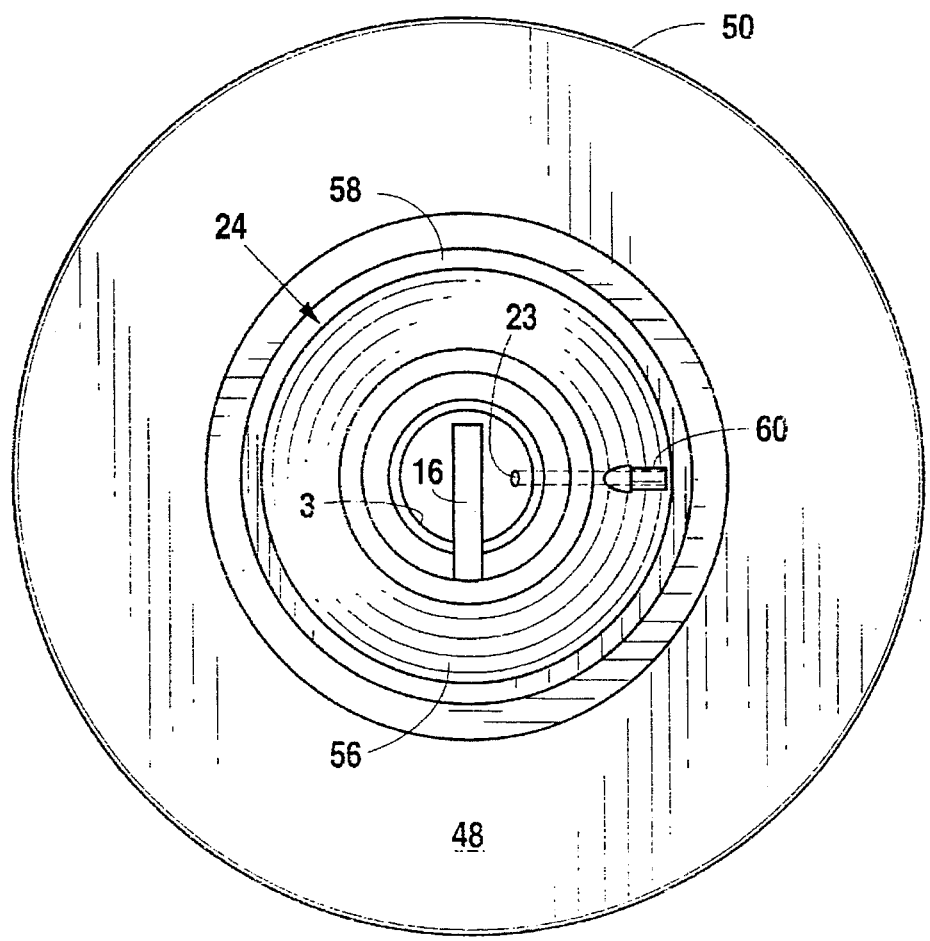
FIG. 2 is a bottom plan view of the first embodiment.
Figure 4:
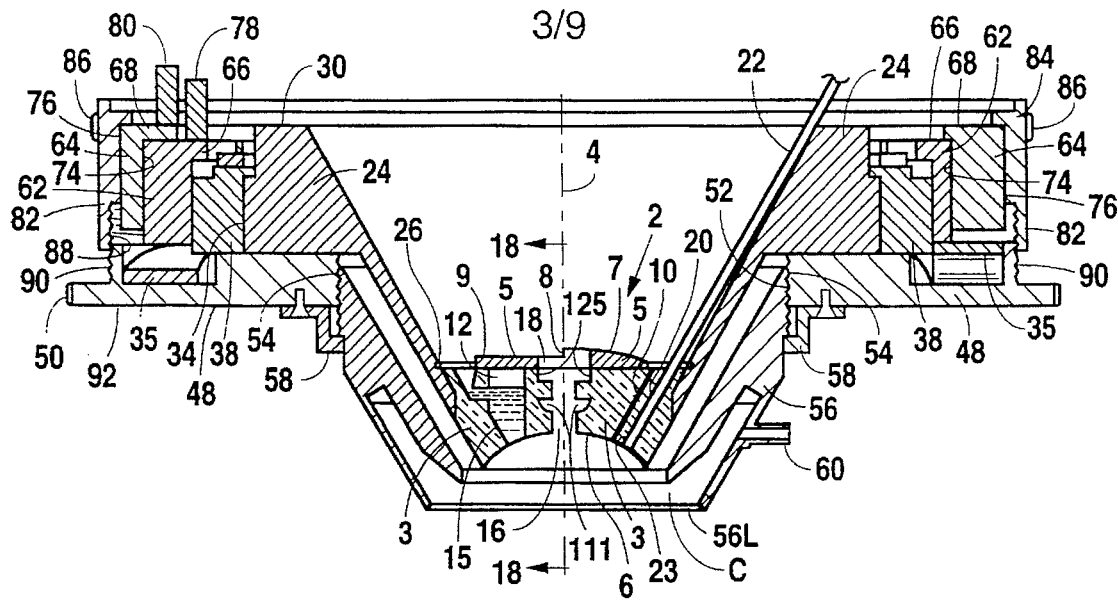
FIG. 4 is a cross sectional view of the first embodiment assembly of the invention; illustrating the lens holder of FIGS. 3A and 3B in operative position in the housing of FIG. 3.
Figure 5:
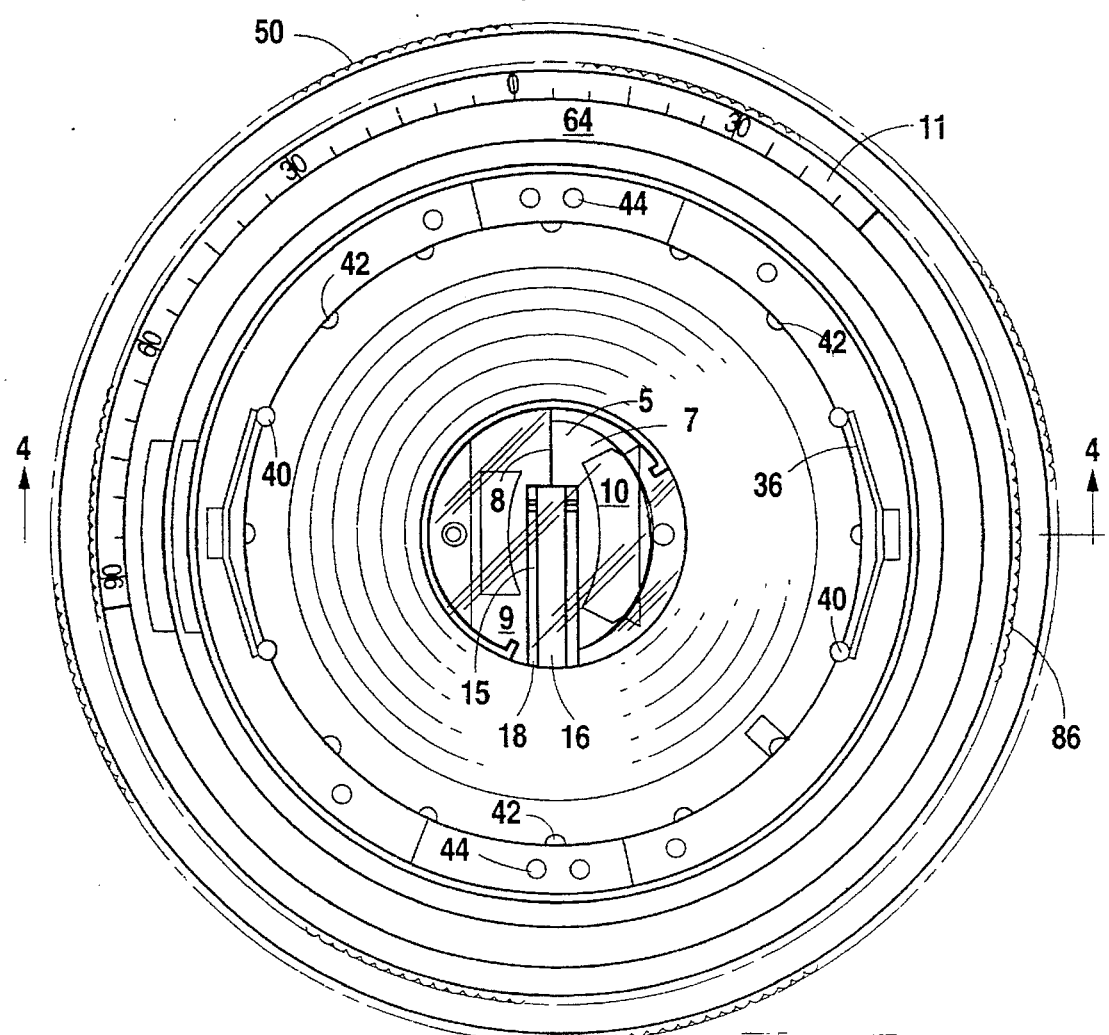
FIG. 5 is a top plan view of the assembly of FIG. 4.

The first embodiment of the invention, which is generally designated 1, comprises an instrument which includes a slotted guide lens 2, FIG. 4, having a central axis 4 which is alignable with the visual axis of an eye and positioned so that a lower, concave spherical surface 6 having a radius of curvature ranging from 7–10 mm fits against the outer surface of the cornea which consequently conforms to the shape of surface 6. The guide lens 2 is formed of a lower lens component 3 (FIG. 4) in general the shape of an inverted, truncated cone and an upper lens component 5 permanently bonded to the lower lens component 3. The right side of the upper lens component 5 is provided with an optically ground curved upper surface 7 as shown in FIG. 4 which terminates at a planar vertical surface 8 aligned with the optical axis 4; it should be noted that the portion of upper component 5 to the left of vertical surface 8 has a planar upper surface 9. An alternative embodiment comprises the lower lens component 3 and upper lens component 5 being symmetrical on both sides of vertical surface 8. A radial slot 16 which is best shown in FIGS. 2, 4 and 5 extends through the lens components 3 and 5 and functions as a scalpel guide for effecting radial surgical incisions in the cornea as the scalpel is moved along the radial slot.

A first planar mirror 10 (FIG. 4) is embedded in the right portion of lens 2 beneath the curved upper surface 7 and has a mirrored aluminized surface facing axis 4 and inclined at 56.5° relative to axis 4. A bottomless reservoir 12 into which a saline solution can be provided by means of a tubular bore or hole 14 is provided in the left portion of the lens along with a second mirror 15 having a mirrored aluminized surface facing axis 4 and inclined at 53.74° angle relative to axis 4. The reservoir 12 is optional and can be omitted if desired. All of the lens components and mirrors are bonded together to provide a unitary lens structure.

It should also be noted that the radial slot 16 is of relatively narrow width sufficient to accept the lower end of a scalpel without permitting substantial transverse movement of the scalpel; however, a wider slot 18 is provided immediately above the more narrow slot 16 to accommodate a portion of a guide sleeve which accepts the lower end of the scalpel. The mirrors 10 and 15 permit the surgeon to visually monitor the incision as it is being made through a microscope (not shown) looking downwardly through guide lens 2 to permit visual verification and control of radial or other incision penetration depth of the scalpel into the cornea. It should be noted that angles other than 53.74° and 56.5° may be used without departing from the scope of the invention provided that the angle selected allows the surgeon to visually monitor the incision.

The lens 2 also has a tubular bore or hole 20 (FIG. 4) extending from the curved upper surface 7 to the lower, concave surface 6 which holds a fiber optic light pipe 22 guide of conventional construction having its upper end connected to a light source (not shown) and having a lower end 23 contiguous with surface 6 for illuminating the cornea during the surgical procedure. The guide lens 2 fits telescopically within an inverted conical lens holder 24 (FIG. 4), which is in the shape of an annular, inverted truncated cone, and in which the lens 2 is secured by a snap ring 26. Lens holder 24 is supported for rotational adjustment about central axis 4 and is also supported for horizontal translational movement in any direction perpendicular to axis 4. Moreover, lens holder 24 is also supported for vertical adjustment in either direction along axis 4. The means for providing the aforementioned adjustments will be discussed in detail hereinafter.

Arcuate cuts are made by rotating the lens assembly as necessary to move the scalpel along the circumference of the cornea. Radial cuts are preceded by rotating the holder assembly 24 into a desired one of 16 radial meridian positions which are easily located by clip and notch assemblies the details of which are to be discussed hereinafter.

Figure 7:
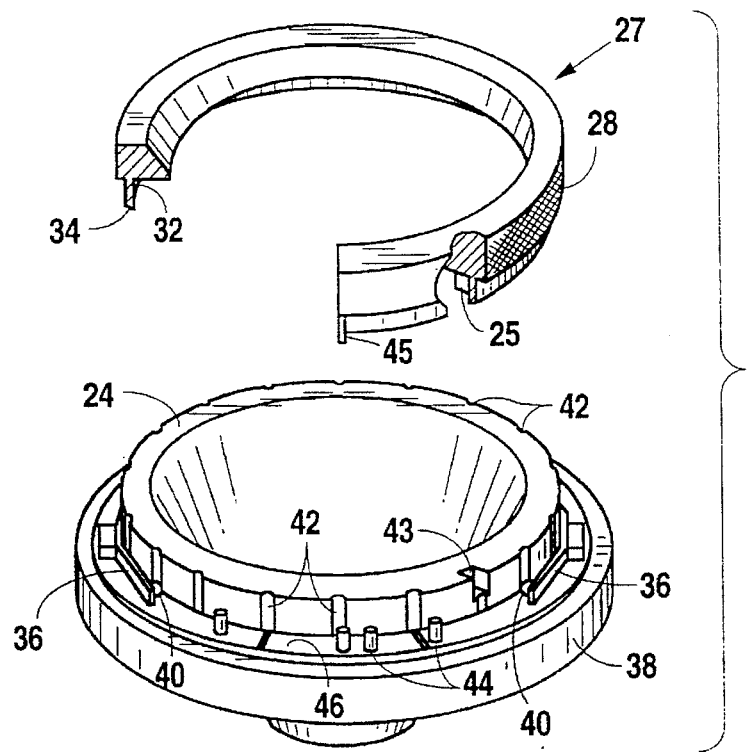
FIG. 7 is a perspective view of the cooperating parts of the assembly which permits limited rotation of the lens holder relative to the housing.
Figure 8:
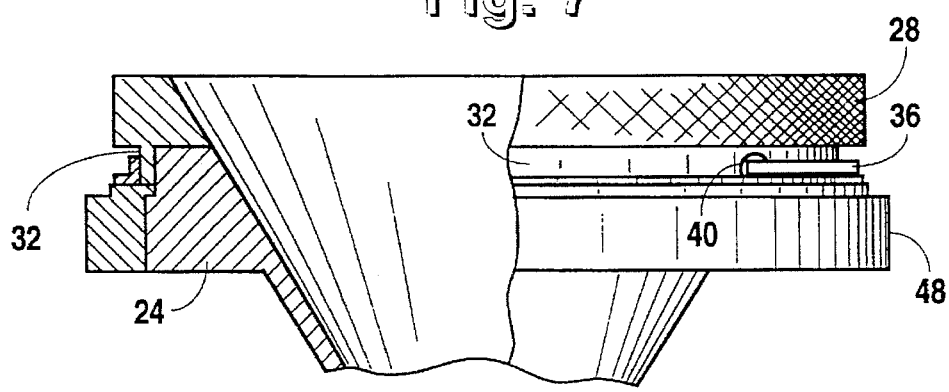
FIG. 8 is a front elevation partially in section of the components of FIG. 7 in assembled condition.
Figure 9:
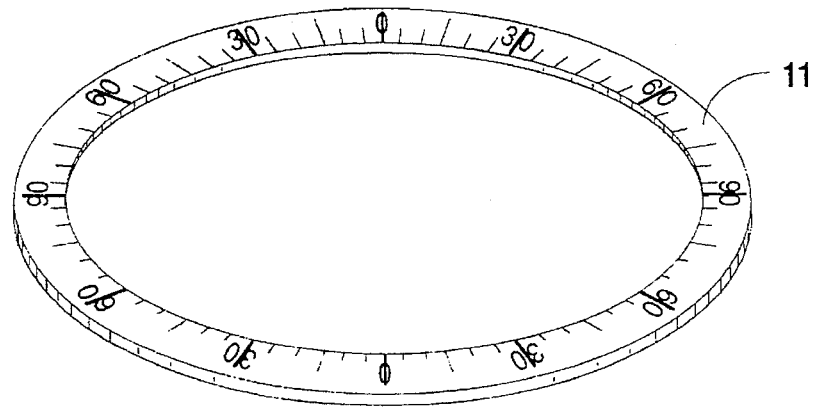
FIG. 9 is a perspective view of a circular indicator means for permitting visual confirmation of the rotary position of the lens.

As shown in FIG. 7, a drive sleeve 27 having a grip surface 28 disposed circumferentially around its upper end can be positioned over lens holder 24 and used to manually rotate conical holder 24 by means of an internal drive lug 25 received in notch 43 in holder 24. A circular radial shield flange 32 is located immediately below the grip surface 28 and has an outer surface 34 parallel to the axis of the instrument as best shown in FIG. 7.

Two equidistantly spaced "V"-shaped clips 36 are provided on the uppermost surface of an orbital detent ring 38 which encircles conical holder 24 with each clip 36 being perpendicular to the instrument's axis 4. A detent ball 40 is provided at each end of clip 36. The circumference of conical guide lens holder 24 is interrupted by a plurality of equidistantly spaced notches or slots 42, preferably 16 in number, each adapted for partially receiving one of balls 40 to releasably hold lens holder 24 in any one of 16 possible positions of rotation. When drive sleeve 27 is in position, shield flange 32 prevents balls 40 from entering slots 42 so that the lens holder 24 can be freely rotated to allow for the making of arcuate incisions. With drive sleeve 27 removed the guide lens 2 can be rotated to a desired one of 16 rotary positions relative to the eye, in each of which radial slot 16 is aligned with one of the notches 42. Thus, incisions made by traversal of a scalpel along slot 16 will likewise be aligned with the notches 42 with which slot 16 is aligned.

Thus, the radial positions marked by notches 42 are used to properly position slot 16 for making desired radial cuts. However, the making of arcuate cuts is more complicated since arcuate cuts cannot be permitted to intersect the radial cuts and must be restricted to that portion of the cornea between adjacent radial cuts. When an operation includes the making of arcuate cuts as well as radial cuts, the radial cuts are only made at radial positions in alignment with every other notch 42, for a total of 8 equally spaced radial cuts. Restriction of the arcuate cuts to the portion of the cornea between these 8 radial cuts is effected by providing a plurality of vertical mechanical stop pegs 44 (FIG. 7) in vertical wells in the uppermost surface 46 of orbital detent ring 38. Stop pegs 44 are spaced an arcuate distance apart (as measured relative to axis 4) that is less than the arcuate distance between two adjacent radial cuts. A radial finger tab 45 extending from outer surface 34 on shield flange 32 of drive sleeve 27 falls in between stop pegs 44 which consequently restrict the length of any arcuate incision to define an arc of slightly smaller angle than that defined by the two notches 42 between which stop pegs 44 are positioned and between which the arcuate incision is effected. Thus, by using the scalpel transversely mounted across guide slot 16 at a desired radial position it is possible to make an arcuate cut by rotation of the guide lens so that the arcuate cut extends between, yet distinct from and not intersecting, adjacent radial cuts. By providing openings on surface 46 of orbital detent ring 38 for receiving stop pegs 44 arcuately inwardly between notches 42, it is possible to make tangent cuts in each of the 8 radial sections of the cornea without intersecting any of the 8 radial cuts that might be made at the borders of these sections.

Figure 3:
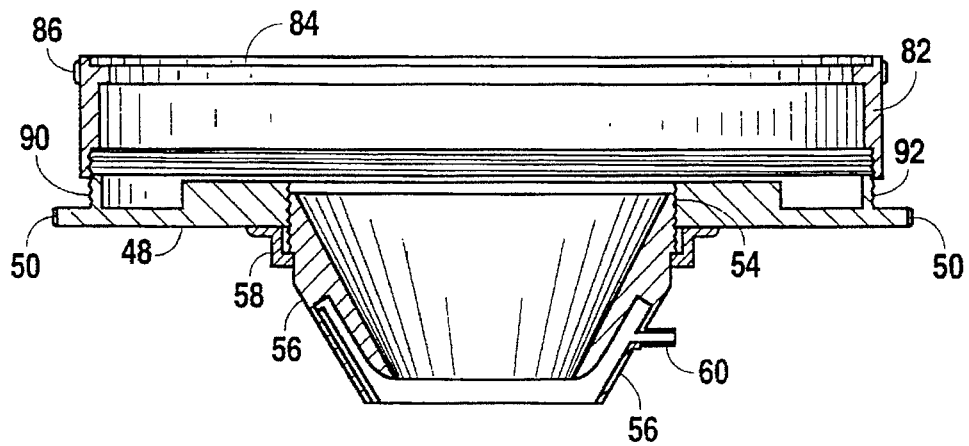
FIG. 3 is a bisecting cross-sectional view of the housing in which the lens support structure of the first embodiment is positionable.
Figure 3A:
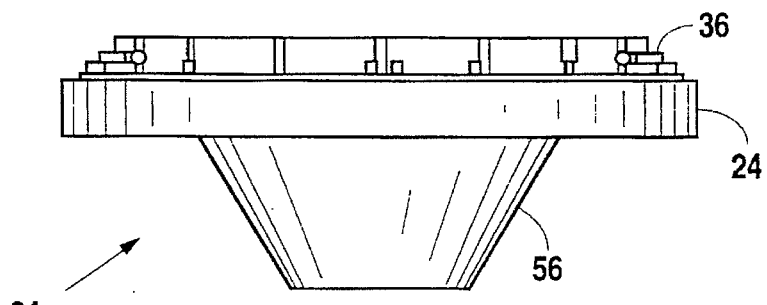
FIG. 3A is a front elevation of the lens holder structure that is positionable in the housing of FIG. 3.
Figure 3B:
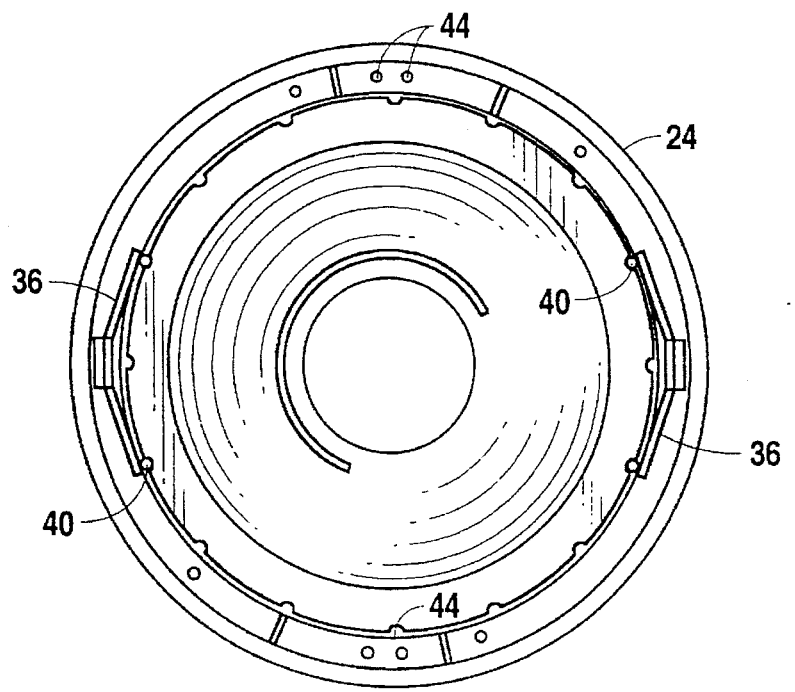
FIG. 3B is a top plan view of the lens holder of FIG. 3A.

It will consequently be apparent from the foregoing that the guide lens 2 and the lens holder 24 must be capable of being rotated to a desired position in which radial slot 16 is properly aligned for effecting a radial incision and the lens holder is locked into position for the radial incision procedure. Similarly, the lens holder 24 must be capable of rotating during an arcuate incision procedure between the limits defined by the stop peg positions as discussed above. The means for effecting and permitting the necessary movement and retention of the lens holder 24 and the associated guide lens 2 is best illustrated in FIGS. 3, 3A and 4 to which reference is made.

Figure 6:
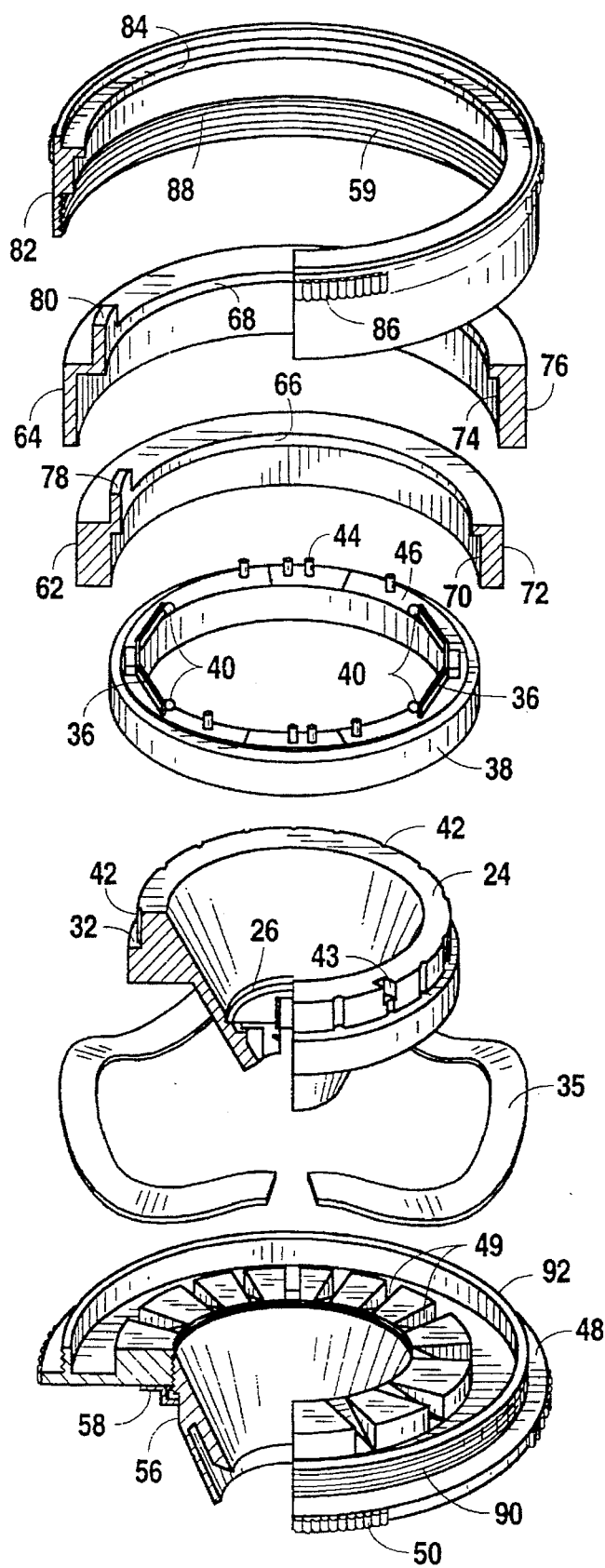
FIG. 6 is an exploded perspective view of the assembly of the first embodiment.

More specifically, the orbital detent ring 38 is supported by a flat, annular support base 48 which has a manual grip surface 50 about its outer periphery for permitting manual rotation. Friction between the contacting surfaces of ring 38 and base 48 and between the contacting surfaces of lens holder 24 and base 48 can be reduced by providing equally spaced radial slots across the contacting surface on base 48—as shown in FIG. 6. Internal thread 52 are provided in base 48 for engagement with threads 54 on the upper end of an annular, inverted truncated vacuum cone 56 which is coaxial with the guide lens 2.

Ring member 58 is an optional component attached to the lower surface of the support base 48 and has a lower end to limit the downward extent of movement of vacuum cone 56 relative to support base 48 so as to prevent support base 48 and vacuum cone 56 from being inadvertently disconnected from each other.

A vacuum source (not shown) is connected to a conventional connector 60 to provide a vacuum to an annular chamber C extending upwardly from the lower end 56L of cone 56 thereby holding the device onto the sclera of the patient.

Since the visual axis of the eye does not always coincide with its geometrical axis, the guide lens 2 and holder 24 are adjustably movable universally in a horizontal plane perpendicular to the axis 4 of the instrument to facilitate aligning the axis of the guide lens 2 with the visual axis of the eye. This is done by two eccentric inner and outer alignment rings 62, 64 (FIGS. 4 and 5) circumferentially positioned in encircling manner around the orbital detent ring 38. The alignment rings 62 and 64, respectively, each contain inwardly directed upper flanges 66 and 68, enabling the inner alignment ring 62 to be supported by the orbital detent ring 38, and the outer alignment ring 64 to be supported by the inner alignment ring 62 as best shown in FIG. 4. The inner alignment ring 62 fits exteriorly and eccentrically around the orbital detent ring 38, and interiorly and eccentrically within the outer alignment ring 64.

Eccentric inner ring 62 has an inner cylindrical surface 70 and an outer cylindrical surface 72 which is axially eccentric relative to surface 70; similarly, outer alignment ring 64 has inner and outer cylindrical surfaces 74 and 76 respectively which are eccentric to each other (i.e. their axes are not concentric but are spaced apart). Consequently, the radial thickness of the wall of each of rings 62 and 64 varies along its circumference as shown by comparison of the right side and left side of the rings in FIG. 4.

Small handles 78 and 80 are respectively located on the upper surfaces of alignment rings 62 and 64 for permitting manual rotation of each ring. The handles 78 and 80 are located on the widest cross section of the inner alignment ring 62, and the thinnest cross section of the outer alignment ring 64, respectively. Controlled rotation of the rings permits universal horizontal adjustment in any direction of orbital detent ring 38, holder 24, and slotted guide lens 2 to a desired position in which the axis 4 of the guide lens is properly aligned with the optic axis eye prior to initiation of the surgical procedure. To insure the movement of the alignment rings is smooth, their contact surfaces can be teflon coated as can be the contacting surfaces of holder 24, orbital detent ring 38 and flat annular support base 48.

Figure 1:
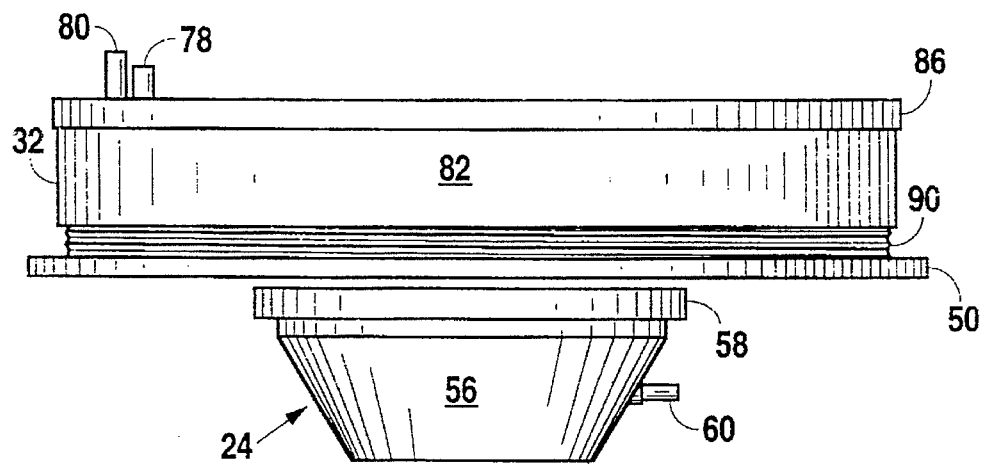
FIG. 1 is a front elevation of a first embodiment of the invention.

An outer lock ring 82 formed of one of several corrosion resistant materials including stainless steel and titanium fits cylindrically and concentrically around the outer alignment ring 64 and has an inwardly disposed clamp flange 84 at its upper end which extends over outer eccentric alignment ring 64, and a knurled grip surface 86 extending about its upper periphery as shown in FIG. 1. The lower inner edge of the lock ring 82 is provided with threads 88 which are threadedly engaged with threads 90 on a threaded support ring 92 extending vertically from the previously mentioned support base 48. Downward tightening of lock ring 82 exerts a downward force on alignment rings 62 and 64, which in turn compress a wave spring 35 which is trapped between alignment rings 62 and 64 and support base 48 (as shown in FIG. 4). Wave spring 35 thereby prevents eccentric alignment rings 62 and 64, lock ring 82, and support base 48 from turning relative to each other, and fixes the axis 4 of the instrument 1 in a desired horizontal position of adjustment for the duration of the surgical procedure. Orbital detent ring 38 remains free to rotate relative to support base 48 for astigmatic position adjustment.

Figure 24:
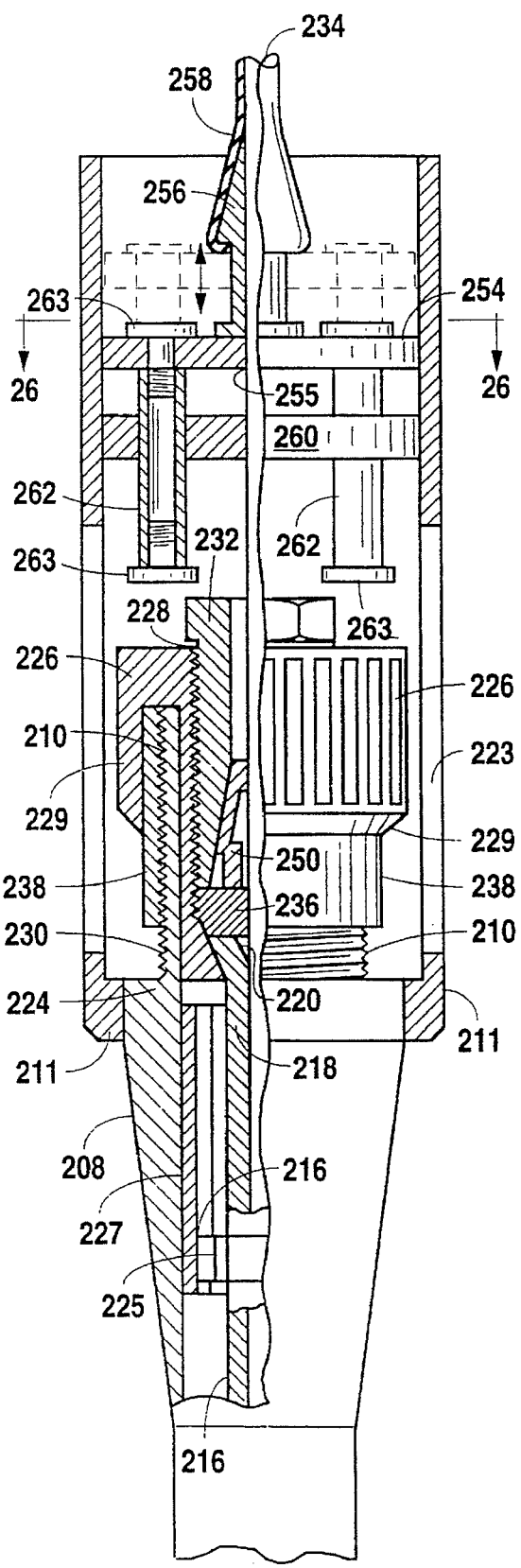
FIG. 24 is a partial sectional view of the upper portion of the second embodiment scalpel of FIG. 23.

The scalpel illustrated in FIGS. 12 and 24 provides a means for a surgeon to adjust the effective depth of incision of a surgical diamond blade 102 used in corneal surgery. More specifically, end 112 of the scalpel fits into a guide sleeve means 104 which fits into radial slots 16 and 18 in lens 2 and thereby guides the scalpel along the slots 16 and 18 for effecting radial surgical incisions in the cornea as the scalpel is moved along the radial slots. Radial slots 16 and 18 are symmetrical about the same radial plane through lens 2, with radial slot 18 being wider than radial slot 16. The upper radial slot 18 intersects the convex surface 7 of lens 2 and extends inwardly to arcuate shoulders 125 (FIG. 18) which define the lower extent of upper slot 18. Radial slot 16 extends downwardly below shoulder 125 to the bottom of lens 2.

The extent of travel of the scalpel along radial slots 16 and 18 is limited by one of a plurality of spacer blocks 105 having different overall lengths. Spacer block 105 is held in place at an end of the radial slots by clamping means consisting of an upwardly biased clamp bar 109 mounted on the lower end of a manipulator rod 300 which can be rotated to position clamp bar 109 parallel to space 111 between shoulders 125 so that the clamp bar can be positioned below the shoulders 125. The clamp bar 109 is then rotated 90° and manipulator rod 300 is released so that spring 107 biases clamp 109 upwardly ataintst the lower wurfaces of shoulders 125. A U-shaped lug 301 on block 105 is consequently urged into mating slots in the upper surfaces of shoulder 125 to prevent movement of block 105.

As shown in FIGS. 19-21, a guide sleeve 123 slidably fits into radial slot 16. Guide sleeve 123 can be square or circular in cross section, depending on whether end 112 of the scalpel is square or circular in cross section. In the first embodiment discussed below guide sleeve 123 is square in cross section in order to prevent the end 112 of the scalpel from turning. A threaded end 113 of guide sleeve 123 supports a curved washer 117 that rests on upper surfaces of shoulders 125. As shown in FIG. 19, curved washer 117 is held in place over end 113 by a lock nut 115. Two wings 119 extend laterally from guide sleeve 123 into grooves 111 (FIG. 4) in lens 2, and serve to guide and retain guide sleeve means 104 in radial slots 16 and 18. When assembling the device, guide sleeve means 104 is positioned in radial slots 16 and 18 and grooves 111 before lens 2 is locked into position in lens holder 24 by snap ring 26. Guide sleeve means 104 remains in lens 2 when the scalpel is removed, and is sterilized along with lens 2 prior to operation.

In a first embodiment 100 (FIG. 10) the scalpel is provided with manual adjustment means 106 for varying the effective cutting length of a surgical diamond blade 102. As shown in FIG. 12, the scalpel has a substantially cylindrical knife housing 108 which has an outer diameter at a first or upper end 110 large enough to be comfortably gripped by a surgeon and a square cross section at a second end 112 which can be readily inserted into guide sleeve means 104 that fits into radial slots 16 and 18 of lens 2.

The larger diameter first end 110 terminates in an externally threaded end portion. An axial bore 114 (FIG. 12) extends the length of knife housing 108 and provides a passageway in which adjustable portions of the scalpel are contained. An elongated, hollow actuator rod 116 is guided along the central axis of knife housing axial bore 114 and serves as a mounting fixture for surgical diamond blade 102.

First or upper end 118 of actuator rod 116 tapers out in a radial direction to form a conical flange 120 as shown in FIG. 12. The second or lower end 121 of actuator rod 116 is square in cross section and is slidably received in second end 112 of knife housing 108 as shown in FIG. 16. Actuator rod 116 is thereby prevented from rotating relative to guide sleeve means 104. A surgical diamond blade 102 is held in second end 121 of actuator rod 116 by one of several means. One embodiment (FIG. 11) shows the second end 121 of the actuator rod 116 crimped inwardly to hold the surgical blade. Another embodiment (FIG. 11A) contemplates holding a surgical diamond blade 102 in the second end 121 of the actuator rod between two L-shaped shims 122 pressed into the second end of the actuator rod and held in place by epoxy.

The cone shaped flange 120 at the upper end 118 of actuator rod 116 is slidably received by an inwardly projecting annular shoulder 124 at the lower end of a thimble 126 (FIG. 12). Thimble 126 has a central axial bore 127, a first internally threaded portion 128 along said axial bore, and a second internally threaded portion 130 spaced radially outwardly from said first internally threaded portion. The second internally threaded portion 130 of thimble 126 is threadedly engaged with the external threads along the upper end 110 of knife housing 108. Second internally threaded portion 130 forms an overhanging portion 129 of thimble 126 which bounds an axially extending annular groove in the thimble. The upper end 110 of the knife housing 108 is received in this annular groove. The number of threads per inch along this second internally threaded portion 130 and along the first end 110 of the knife housing is chosen in order to provide for a fine adjustment in the axial displacement of actuator rod 116.

The first internally threaded portion 128 of the thimble 126 engages with external threads on an adjustment bushing 132 having a central axial bore. A fiber optic cable 134 has an upper or outer end connected to a light source 135 and a lower extent which passes through the central axial bore of the adjustment bushing 132 and then steps down to a smaller diameter cable which passes through the hollow portion along the axis of actuator rod 116. Cable 134 terminates at a point adjacent lower end 121 of the actuator rod so as to provide illumination at the surgical diamond blade 102 held in the second end of the actuator rod. Light passes through the fiber optic cable and then through the diamond blade held in the second end of the actuator rod. This illumination means, along with the fiber optic light pipe 22 that passes through the lens 2, facilitates the control of incision depth achieved when visually monitoring the incision in two mirrors 10 and 15 located within the guide lens 2.

An adjustment of the effective length of knife blade 102 extending from knife housing 108 is achieved by turning the thimble 126 relative to the knife housing 108. The conical flange 120 of actuator rod 116 is trapped against the inwardly tapered annular shoulder 124 at one end of thimble 126 by the adjustment bushing 132 and a clearance washer 136 positioned in between the adjustment bushing and conical flange 120. Adjustment bushing 132 is threadedly engaged with the first internally threaded portion 128 of the thimble 126. The adjustment bushing is tightened into the central axial bore of the thimble until it has pressed the clearance washer against the inwardly projecting annular shoulder 124 of the thimble. The clearance washer is stopped by the inwardly projecting annular shoulder of the thimble, maintaining a small axial clearance above the conical flange 120 at the first end 118 of actuator rod 116. This clearance enables free rotation of the first end 118 of the actuator rod relative to the thimble.

When thimble 126 is turned in a clockwise direction, adjustment bushing 132 and clearance washer 136 turn with the thimble as a unit. Clockwise rotation of the thimble moves the thimble down onto the externally threaded first end 110 of the knife housing, thereby moving the actuator rod 116 towards the second end 112 of the knife housing and extending the knife blade 102 from the knife housing. Counter-clockwise rotation of the thimble and the adjustment bushing as a unit retracts the actuator rod towards the first end 110 of the knife housing, thereby retracting the knife blade.

As shown in FIG. 12, the fiber optic cable 134 extending along the axis of the thimble/adjustment bushing assembly and along the axis of the knife housing, is in two pieces. A larger diameter portion of the fiber optic cable extends along the axial bore of the adjustment bushing and terminates at a point adjacent the first end 118 of the actuator rod. A second smaller diameter portion of the fiber optic cable approximates the end of the larger diameter portion and extends along the axial bore through the actuator rod to a point adjacent the second end 121 of the actuator rod. A sleeve 180 made from one of several possible materials including Kevlar, polyurethane, and PVC encase fiber optic cable 134. Sleeve 180 terminates at a restraint cap 182 threadedly engaged with one end of the adjustment bushing thereby providing a strain relief.

A relatively fine thread (40–100 threads per inch APE) is provided along the first end 110 of knife housing 108 and engaging portion 128 of the thimble 126. The difficulty in machining this fine thread on the radially inner side of overhanging portion 129 of thimble, 126 necessitates forming this threaded portion of the thimble as a separate member in the form of a thimble bushing 138. After thimble bushing 138 is internally threaded with the required fine threads, thimble bushing 138 can be brazed or silver soldered into the axially extending annular groove formed in the thimble by the radially outer overhanging portion 129.

Figure 23:
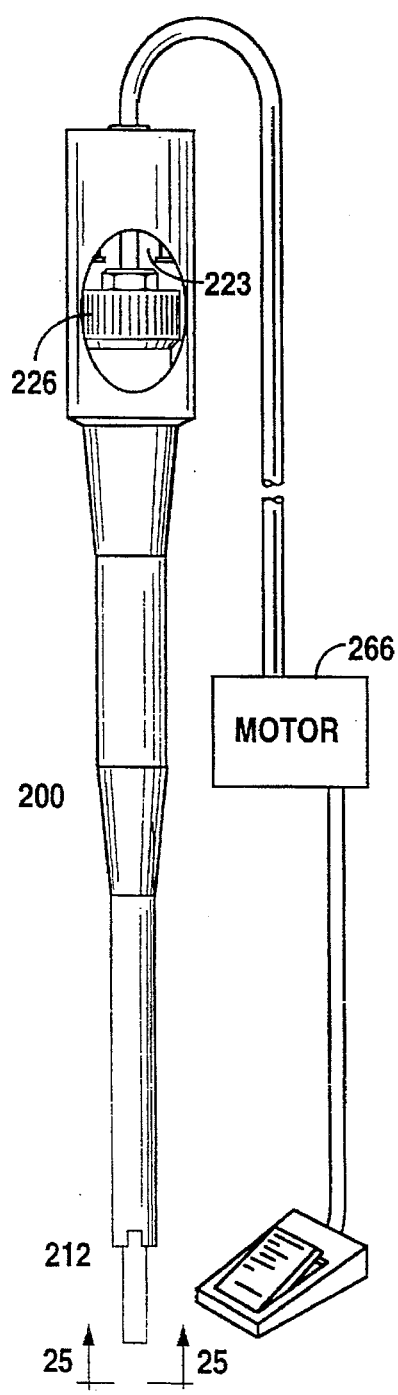
FIG. 23 is a perspective view of a second embodiment scalpel means usable with the structure disclosed in FIGS. 1–9.

A second embodiment of the scalpel is shown in FIGS. 23 and 24. This embodiment provides a means for motorized extension and retraction of the surgical blade from one end of the scalpel. In this embodiment a fiber optic cable 234 serves two purposes: as an illumination means, and as a driving means for the thimble 226 and in turn the actuator rod 216. As with the first embodiment, the knife housing 208 is in an elongated form for easy gripping by a surgeon. A first end of the knife housing 210 is provided with external threads and a second end of the housing 212 is slidably received in guide sleeve means 104 that is in turn guided within grooves 16 and 18 in lens 2 in the manner of the first embodiment.

The externally threaded first end 210 of the knife housing extends into a thimble housing 211 which is fixed to the periphery of the knife housing at the base of the threaded portion. Thimble housing 211 surrounds a thimble 226 threadedly engaged with the threaded portion at the first end 210 of the knife housing and is provided with radial openings 223 therethrough for access to the thimble.

A central axial bore is provided in the knife housing and an elongated hollow actuator rod 216 is nonrotatably guided within the central axial bore of the knife housing. A first end of actuator rod 216 tapers out to a cone shaped flange 220. The second end 221 actuator rod 216 has means for holding a surgical diamond blade 102. As shown in FIGS. 27–29, a key way collar 225 is fixed to the outer diameter of this actuator rod at a point in between the first and second ends. Key way collar 225 has lateral protrusions 231 (FIG. 28) which are slidably engaged with grooves in a key way bushing 227 pressed into the central axial bore of knife housing 208.

Thimble 226 is threadedly engaged with the first end 210 of the knife housing and is provided with a first internally threaded portion 228 and a radially outer second internally threaded portion 230. These two internally threaded portions of the thimble are concentric with each other and with the central axis of the knife housing.

An externally threaded adjustment bushing 232 engages with the first internally threaded portion 228 of the thimble. The second internally threaded portion 230 of the thimble engages with the threaded first end 210 of the knife housing 208. As with the first embodiment, the difficulty in machining fine threads on the radially inner side of an overhanging portion 229 of thimble 226, necessitates providing second internally threaded portion 230 as a separate thimble bushing 238 that can be silver soldered or brazed to the thimble 226.

The fiber optic cable 234 passes through a central axial bore in the adjustment bushing 232 and through the central axial bore of the actuator rod 216, terminating at a point adjacent the second end 221 of the actuator rod 216. In the second embodiment of the scalpel, means are provided for fixing cable 234 relative to the adjustment bushing/thimble assembly. This means comprises a tapered flexible collet 250 positioned around cable 234 and inside a central axial bore through the adjustment bushing 232. Flexible collet 250 is engaged by a corresponding tapered portion 252 on adjustment bushing 232.

Conical flange 220 at the first end of actuator rod 216 is trapped by an inwardly tapered annular shoulder 224 at one end of the thimble. A clearance washer 236 is provided between first end 218 of the actuator rod 216 and the adjustment bushing 232. Clearance washer 236 rests against annular shoulder 224 in thimble 226 and provides a surface against which collet 250 rests. When adjustment bushing 232 is tightened into the thimble, tapered surface 252 presses the collet axially against the clearance washer and radially against the cable. Therefore, a friction connection is provided between cable 234 and adjustment bushing 232. Axial forces generated by tightening adjustment bushing 232 against clearance washer 236 in the axial bore of thimble 226 maintain the adjustment bushing and the thimble in fixed relationship relative to each other.

First end 218 of actuator rod 216 is free to rotate relative to annular shoulder 224 in thimble 226 because axial forces generated by tightening adjustment bushing 232 into thimble 226 are resisted by the clearance washer which rest against annular shoulder 224 in the thimble. Therefore, as cable 234 is rotated, adjustment bushing 232 and thimble 226 rotate together as a unit. Rotation of the thimble results in axial travel of the thimble, and hence the actuator rod, relative to knife housing 208. As shown in FIG. 24, actuator rod 216 is prevented from rotating relative to knife housing 208 by the engagement of key way collar 225 with the key way bushing 227.

Alignment of the cable with the central axis of the knife housing is assured by the provision of a trailing plate 254 that slidably engages with an internal diameter of thimble housing 211 at a point axially spaced from adjustment bushing 232. As shown in FIGS. 24 and 26, trailing plate 254 has a central bore 255 through which cable 234 passes, and has a nipple 256 for engagement with a sleeve 258 made from one of several materials including Kevlar, polyurethane, and PVC is provided around fiber optic cable 234. A spacer plate 260 is provided parallel to this trailing plate 254 and between trailing plate 254 and adjustment bushing 232. Spacer plate 260 is fixed to the internal diameter of thimble housing 211. A plurality of linear bushings 262 are attached at right angles to trailing plate 254 by bushing screws 263 and are slidably engaged with respective axial bores 265 through spacer plate 260. As cable 234 is rotated, and hence moved in an axial direction along with the thimble/adjustment bushing assembly, trailing plate 254 assures that cable 234 will remain in alignment with the central axis of knife housing 208 and prevents binding of the cable as it moves in and out of the knife housing.

As shown in FIG. 23, a stepper motor 266 is provided in the second embodiment for rotating cable 234. The degree of control of motor rotation required is determined by the degree of control of axial extension and retraction of the surgical blade desired by a surgeon. The degree of control of axial extension and retraction of the blade is in turn a function of the number of threads per inch provided on the thimble second internally threaded portion 230 and on the first end 210 of knife housing 208. Therefore, selection of a stepper motor is related to the number of threads per inch provided on the threadedly engaged portions of knife housing 208 and thimble 226.

The entire device is normally hand held during the surgical procedure; however, mechanical support means could be used if desired.

It should be understood that the invention is not limited to the specific device as shown and that the spirit and scope of the invention extends to obvious variations that will be apparent to those of skill in the art and should therefore be defined solely by the appended claims.

What is claimed is:

1. A scalpel for performing corneal surgery, said scalpel comprising:
    a) a knife housing substantially cylindrical in shape for easy gripping by a surgeon, said knife housing having a first end, a second end, a central axis, and an axial bore passing therethrough, said first end being externally threaded along an axial extent thereof,
    b) an actuator rod guided concentrically within said knife housing axial bore, said actuator rod having a first end, a second end, and an axial bore passing therethrough, with said first end flared out in the shape of a cone,
    c) a surgical blade and holding means for securing said surgical blade in said second end of said actuator rod,
    d) a cable extending along said knife housing central axis through said actuator rod axial bore from said actuator rod first end to a point in said actuator rod axial bore adjacent said actuator rod second end,
    e) an adjustment bushing surrounding a portion of said cable, said adjustment bushing being externally threaded, and f) thimble means for adjusting an axial position of said actuator rod relative to said knife housing, wherein said thimble means has a radially inner cylindrical portion having an axial bore therethrough and internal threads, a radially outer overhanging portion bounding an axially extending annular groove in said thimble means, said annular groove receiving the first end of the knife housing therein and said inner cylindrical portion threadedly engaged with said adjustment bushing and flared radially inwardly towards a central axis of said thimble means at an end of said thimble means which matingly receives the cone-shaped end of the actuator rod.

2. The scalpel of claim 1 wherein the cable is a fiber optic cable.

3. The scalpel of claim 2 wherein a portion of the cable extending outside of said knife housing is encased in a kevlar sleeve, and said sleeve terminates at a holding means for relieving stresses in said sleeve.

4. The scalpel of claim 2 wherein said holding means for securing said surgical blade comprises two L-shaped shims positioned in the second end of the actuator rod, one shim on each side of the surgical blade and epoxy glue filling the second end of the actuator rod around the blade and the shims.

5. The scalpel of claim 2 further including a thimble bushing, wherein said thimble bushing is integral with said thimble means, and said thimble bushing is threadedly engaged with the externally threaded first end of the knife housing.

6. The scalpel of claim 2 further including a clearance washer positioned around said cable and between said adjustment bushing and said actuator rod first end whereby clockwise rotation of said adjustment bushing presses said clearance washer against the thimble means inwardly flared portion.

7. The scalpel of claim 2 further including a guide sleeve into which said knife housing second end is slidably received, said guide sleeve being externally threaded over a portion of its length, having lateral protrusions for engaging with a guide slot in a lens, and having a curved washer held in position around said externally threaded portion by a lock nut threadedly engaged with said externally threaded portion.

8. A hand-held device for adjustably positioning a surgical blade, wherein said device comprises:

a) a main housing shaped for comfortable gripping by a surgeon, said main housing having a first end, a second end, a central axis, and an axial bore passing therethrough, said first end being externally threaded along an axial extent thereof, b) an actuator rod guided concentrically and non-rotatably within said main housing axial bore and having a first end, a second end and an axial bore passing therethrough, with said first end flared out in the shape of a cone, c) holding means for securing the surgical blade in said second end of said actuator rod, d) a cable extending along said main housing central axis through said actuator rod axial bore from said actuator rod first end to a point in said actuator rod axial bore adjacent said actuator rod second end, e) an adjustment bushing concentric with and surrounding a portion of said cable, friction means for maintaining said adjustment bushing in fixed relationship with said cable, said adjustment bushing being externally threaded, f) thimble means for adjusting an axial position of said actuator rod relative to said main housing, said thimble means having an axial bore, a first internally threaded portion along said axial bore engaged with the adjustment bushing external threads, a second internally threaded portion spaced radially outwardly from said first internally threaded portion and engaged with said main housing external threads, and an inwardly projecting annular shoulder at one end of said thimble means axial bore for slidably engaging the cone-shaped first end of the actuator rod, g) a thimble housing substantially cylindrical in shape, fixed to an outer periphery of said main housing adjacent said threaded extent of said main housing first end, said thimble housing surrounding said thimble means and having radial openings therethrough for providing access to said thimble means, and h) power means for controllably rotating said cable.

9. The device of claim 8 further including a key way bushing pressed into said housing axial bore, a key way collar fixed to said actuator rod, and said key way collar slidably received in a longitudinal groove in said key way bushing.

10. The device of claim 9 further including a spacer plate fixed inside said thimble housing, said spacer plate having a central bore therethrough for allowing passage of the cable, a plurality of circumferentially spaced bores located at a radius from said central bore, a trailing plate slidably mounted in the thimble housing parallel to said spacer plate and having a plurality of linear bushings fixed at right angles to said trailing plate, said linear bushings slidably received in said spacer plate circumferentially spaced bores, and said trailing plate having a central extending nipple through which the cable passes and providing a terminating point for a sleeve around said cable.

11. The device of claim 9 wherein said friction means comprises a flexible collet surrounding said cable and wedged against a tapered portion of an axial bore through said adjustment bushing, whereby turning the adjustment bushing in a clockwise direction relative to the thimble means compresses the collet radially inwardly against the cable, and wherein the thimble means second internally threaded portion comprises a separate thimble bushing fixed to said thimble means.

12. The device of claim 11 further including a clearance washer surrounding said cable, disposed between said collet and said actuator rod first end, and resting against said thimble means inwardly projecting annular shoulder, whereby said clearance washer allows the thimble means to turn freely relative to the actuator rod when the adjustment bushing is tightened against the collet.

13. The device of claim 8 wherein the cable is a fiber optic cable.

14. The device of claim 13 further including a key way bushing pressed into said housing axial bore, a key way collar fixed to said actuator rod, and said key way collar slidably received in a longitudinal groove in said key way bushing.

15. The device of claim 14 further including a spacer plate fixed inside said thimble housing, said spacer plate having a central bore therethrough for allowing passage of the cable, a plurality of circumferentially spaced bores located at a radius from said central bore, a trailing plate slidably mounted in the thimble housing parallel to said spacer plate and having a plurality of linear bushings fixed at right angles to said trailing plate, said linear bushings slidably received in said spacer plate circumferentially spaced bores, and said trailing plate having a central extending nipple through which the cable passes and providing a terminating point for a sleeve around said cable.

16. The device of claim 8 wherein the cable is a fiber optic cable and further including a key way bushing pressed into said housing axial bore, a key way collar fixed to said actuator rod, and said key way collar slidably received in a longitudinal groove in said key way bushing; and a spacer plate fixed inside said thimble housing, said spacer plate having a central bore therethrough for allowing passage of the cable, a plurality of circumferentially spaced bores located at a radius from said central bore, a trailing plate slidably mounted in the thimble housing parallel to said spacer plate and having a plurality of linear bushings fixed at right angles to said trailing plate, said linear bushings slidably received in said spacer plate circumferentially spaced bores, and said trailing plate having a central extending nipple through which the cable passes and providing a terminating point for a sleeve around said cable.

17. The device of claim 16 wherein said holding means for securing said surgical blade comprises two L-shaped shims positioned in the second end of the actuator rod, one shim on each side of the surgical blade and epoxy glue filling the second end of the actuator rod around the blade and the shims.

18. The device of claim 16 further including a guide sleeve into which said knife housing second end is slidably received, said guide sleeve being externally threaded over a portion of its length, having lateral protrusions for engaging with a guide slot in a lens, and having a curved washer held in position around said externally threaded portion by a lock nut threadedly engaged with said externally threaded portion.

* * * * *